(12) United States Patent
Akimoto et al.

(10) Patent No.: US 12,716,878 B2
(45) Date of Patent: Aug. 25, 2026

(54) SENSOR AND SENSOR SYSTEM

(71) Applicant: KABUSHIKI KAISHA TOSHIBA, Tokyo (JP)

(72) Inventors: Yosuke Akimoto, Yokohama Kanagawa (JP); Akira Fujimoto, Kawasaki Kanagawa (JP); Hiroaki Yamazaki, Yokohama Kanagawa (JP)

(73) Assignee: KABUSHIKI KAISHA TOSHIBA, Kawasaki (JP)

( * ) Notice: Subject to any disclaimer, the term of this patent is extended or adjusted under 35 U.S.C. 154(b) by 605 days.

(21) Appl. No.: 18/173,848

(22) Filed: Feb. 24, 2023

(65) Prior Publication Data

US 2024/0011959 A1 Jan. 11, 2024

(30) Foreign Application Priority Data

Jul. 8, 2022 (JP) ................................ 2022-110262

(51) Int. Cl.
*G01N 33/00* (2006.01)

(52) U.S. Cl.
CPC ................................ *G01N 33/0009* (2013.01)

(58) Field of Classification Search
CPC .................................................. G01N 33/0009
See application file for complete search history.

(56) References Cited

U.S. PATENT DOCUMENTS 9,709,425 B2 * 7/2017 Matsui ................... G01D 11/24
10,859,523 B2 * 12/2020 Yamashita ............. G01N 27/12
2006/0048562 A1 * 3/2006 Oishi ................... G01N 33/006 73/23.2
2009/0074619 A1 * 3/2009 Akechi ............. G01N 33/1846 422/69
2020/0209183 A1 * 7/2020 Jian .................... G01N 33/0009
2022/0260538 A1 * 8/2022 Schaller ............... G01N 33/005

FOREIGN PATENT DOCUMENTS

JP 2007-309905 A 11/2007
JP 2008-51627 A 3/2008
JP 2016-24797 A 2/2016
JP 2021-121910 A 8/2021

OTHER PUBLICATIONS

Japan Patent Office, Office Action in JP App. No. 2022-110262 (Jul. 8, 2025).

* cited by examiner

*Primary Examiner* — Kristina M Deherrera
*Assistant Examiner* — Jean F Morello
(74) *Attorney, Agent, or Firm* — Finnegan, Henderson, Farabow, Garrett & Dunner, LLP

(57) ABSTRACT

According to one embodiment, a sensor includes a housing and a sensor portion. The housing includes a first housing member. The first housing member includes an opening. The sensor portion is provided in the housing. The sensor portion includes a sensor member including a hole, and a sensor element. A first space between the sensor element and the sensor member is connected to a second space that is another space in the housing. A detection target gas is configured to flow into the first space through the opening and the hole.

19 Claims, 6 Drawing Sheets

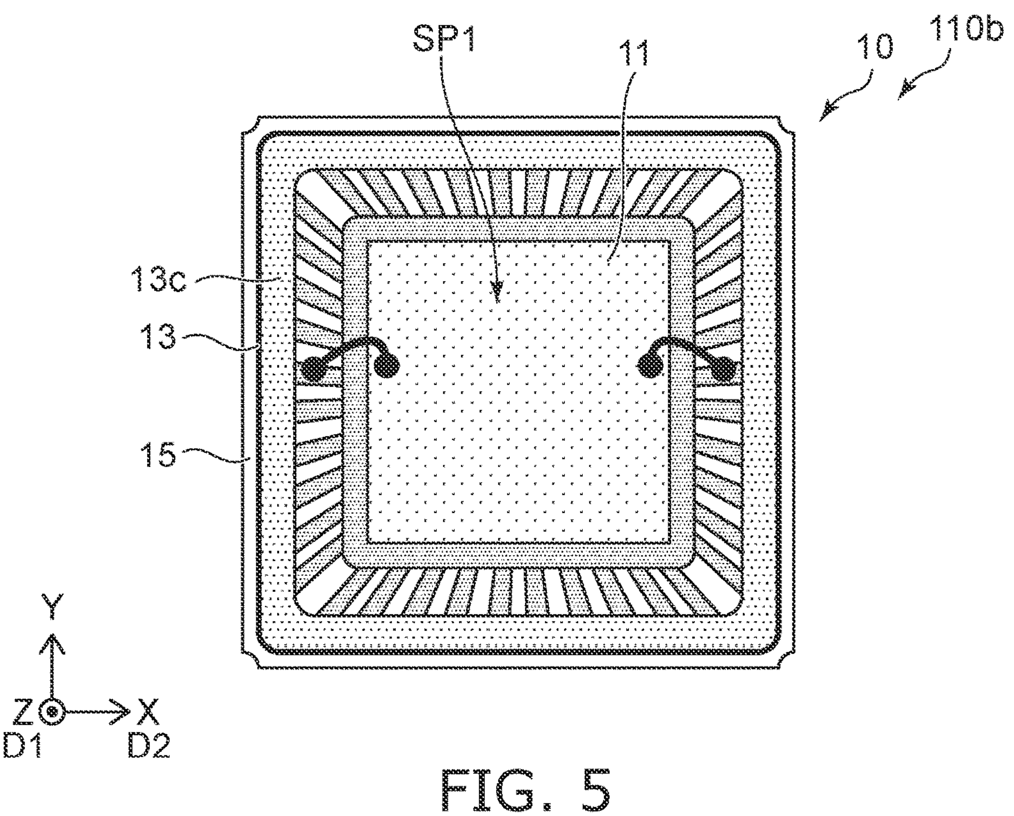
FIG. 5
FIG. 6
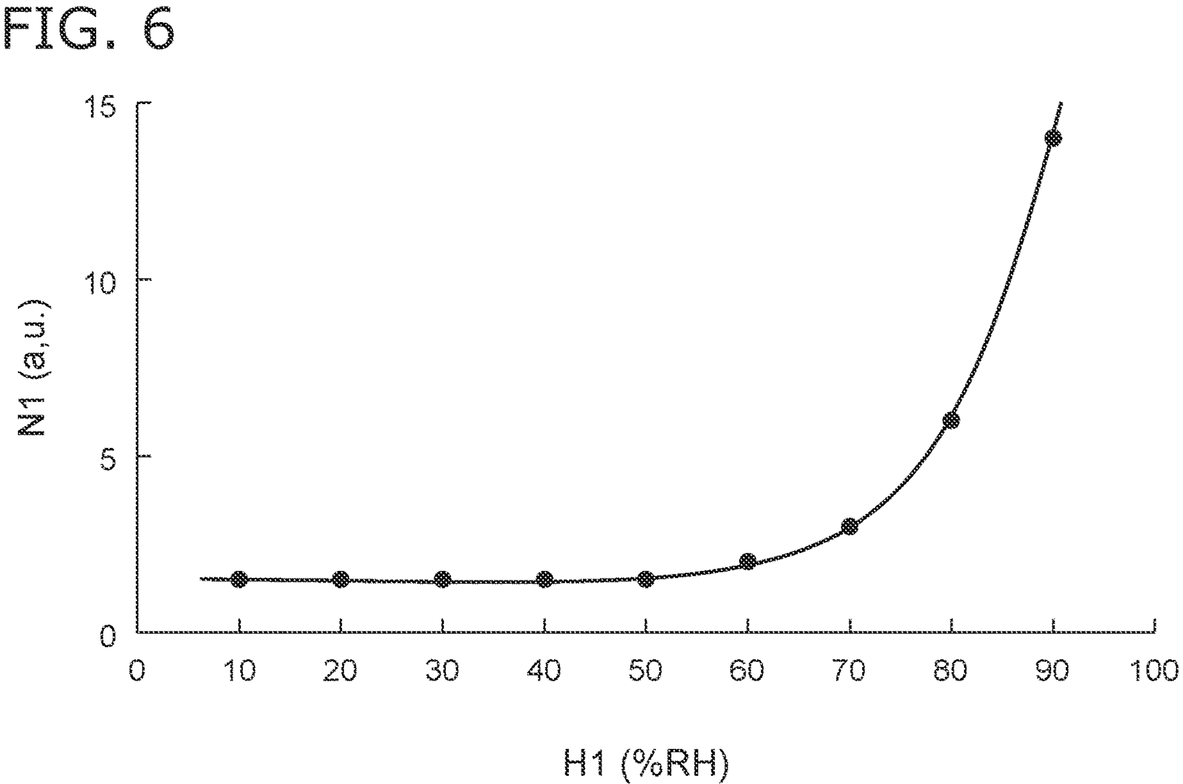

FIG. 7
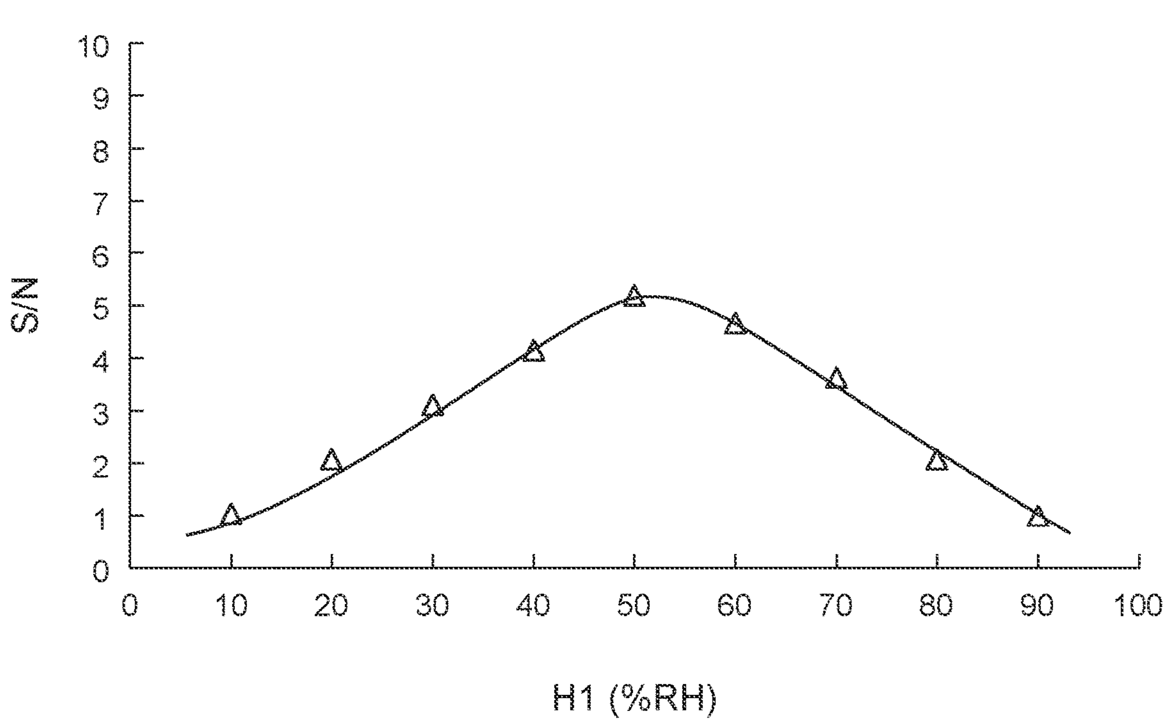
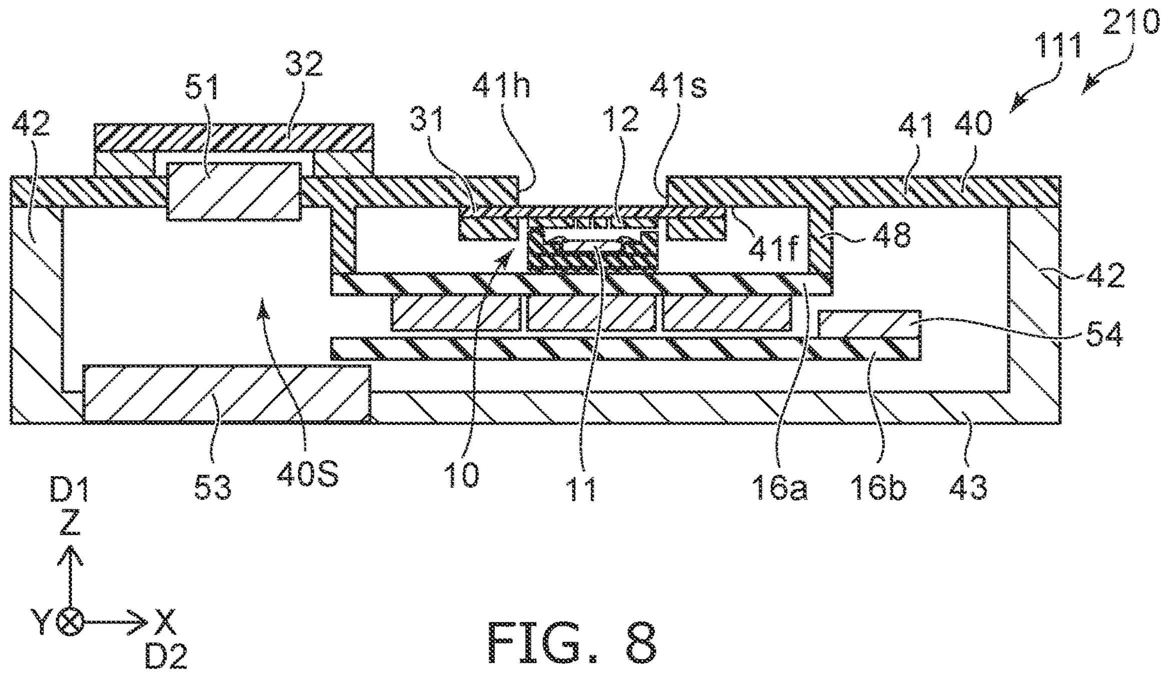
FIG. 8

SENSOR AND SENSOR SYSTEM

CROSS-REFERENCE TO RELATED APPLICATIONS

This application is based upon and claims the benefit of priority from Japanese Patent Application No. 2022-110262, filed on Jul. 8, 2022; the entire contents of which are incorporated herein by reference.

FIELD

Embodiments of described herein generally relate to a sensor and a sensor system.

BACKGROUND

Improvements in detection accuracy are desired in gas sensors and the like.

BRIEF DESCRIPTION OF THE DRAWINGS

FIG. 5 is a schematic plan view illustrating a part of a sensor according to the first embodiment;

FIG. 6 is a graph illustrating characteristics of a sensor;

FIG. 7 is a graph illustrating sensor characteristics;

FIG. 8 is a schematic cross-sectional view illustrating the sensor according to the first embodiment.

DETAILED DESCRIPTION

Figure 1:
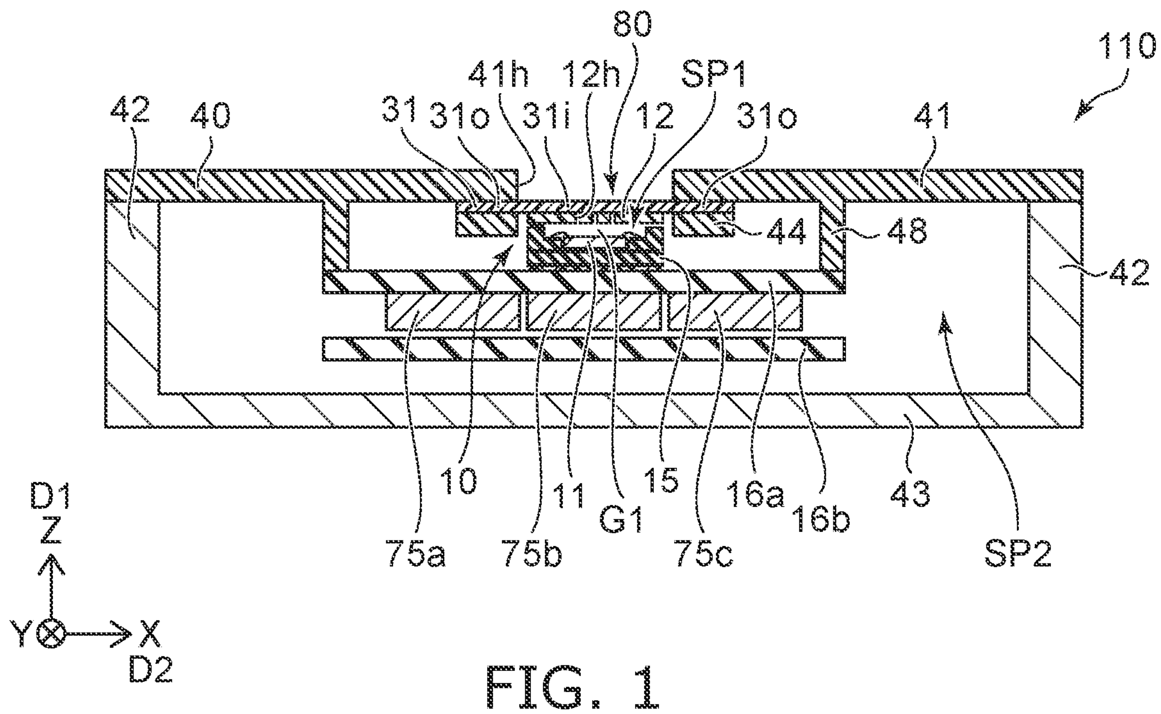
FIG. 1 is a schematic cross-sectional view illustrating a sensor according to a first embodiment.

According to one embodiment, a sensor includes a housing and a sensor portion. The housing includes a first housing member. The first housing member includes an opening. The sensor portion is provided in the housing. The sensor portion includes a sensor member including a hole, and a sensor element. A first space between the sensor element and the sensor member is connected to a second space that is another space in the housing. A detection target gas is configured to flow into the first space through the opening and the hole.

Embodiments of the present invention will now be described with reference to the drawings.

The drawings are schematic or conceptual, and the relationship between the thickness and width of the respective portions, the ratio of the sizes between the portions, and the like are not necessarily the same as the actual ones. Even when the same part is represented, the dimensions and proportions of each other may be represented differently depending on the drawings.

In the specification of the present application and each of the figures, elements similar to those described above with respect to the previously described figures are denoted by the same reference numerals and a detailed description thereof is omitted as appropriate.

First Embodiment

FIG. 1 is a schematic cross-sectional view illustrating a sensor according to the first embodiment.

Figure 2:
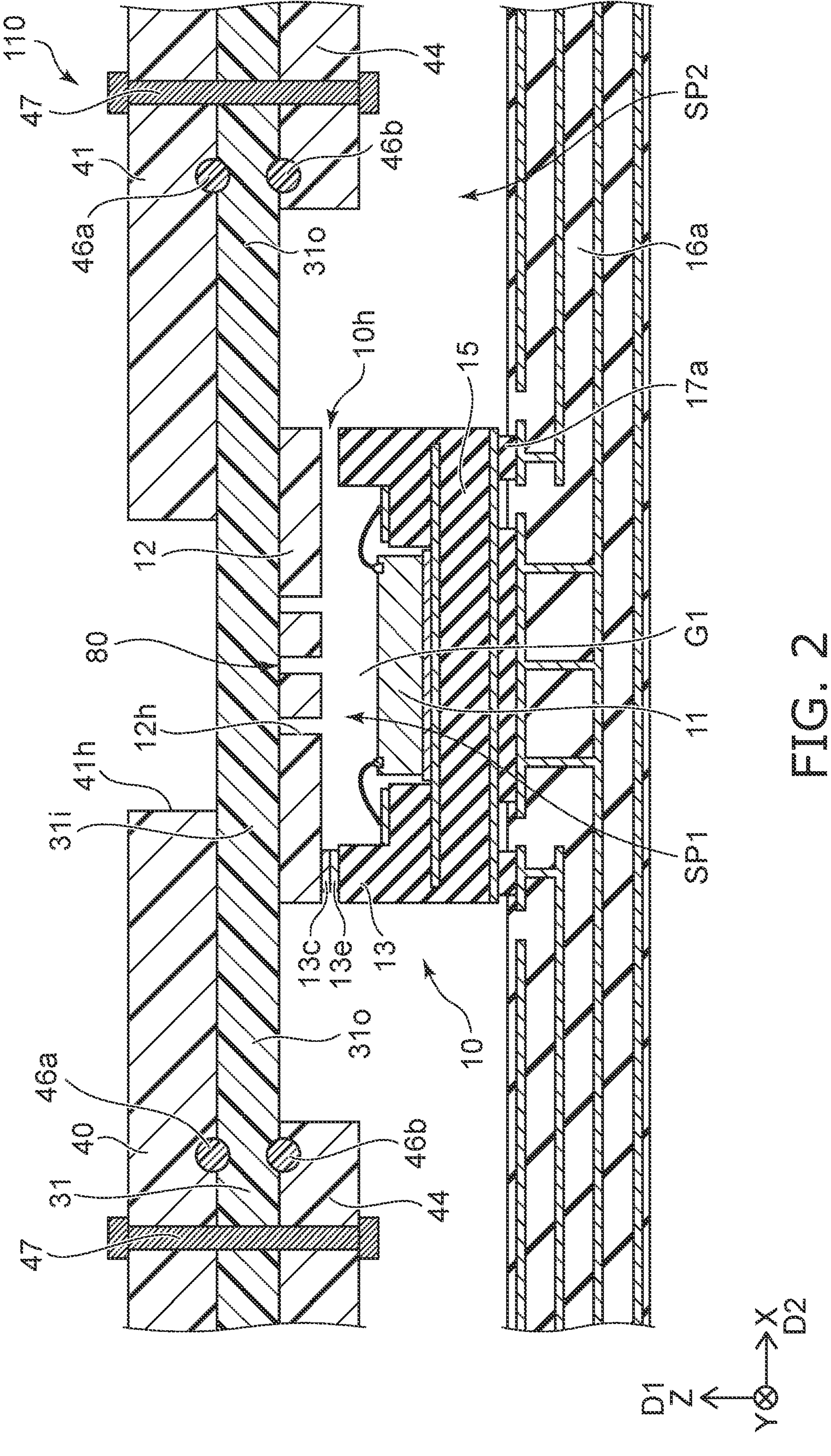
FIG. 2 is a schematic cross-sectional view illustrating a part of the sensor according to the first embodiment.

FIG. 2 is a schematic cross-sectional view illustrating a part of the sensor according to the first embodiment.

FIG. 2 is an enlarged view of a part of FIG. 1. As shown in FIGS. 1 and 2, a sensor 110 according to the embodiment includes a housing 40 and a sensor portion 10.

The housing 40 includes a first housing member 41. The first housing member 41 includes an opening 41*h*.

The sensor portion 10 is provided inside the housing 40. The sensor portion 10 includes a sensor element 11 and a sensor member 12. The sensor member 12 includes a hole 12*h*. The sensor member 12 is, for example, a lid.

A first space SP1 between the sensor element 11 and the sensor member 12 is connected with a second space SP2. A first gap G1 is provided between the sensor element 11 and the sensor member 12. The first space SP1 includes the first gap G1. The second space SP2 is another space inside the housing 40. For example, the space inside the housing 40 includes the first space SP1 and the second space SP2. The space in housing 40 may further include other spaces. The detection target gas 80 can flow into the first space SP1 through the opening 41*h* and the hole 12*h*.

The detection target gas 80 that has flowed into the first space SP1 is detected by the sensor element 11. In the embodiment, the first space SP1 is connected with the second space SP2. As a result, the change in the state of the first space SP1 is reduced by the second space SP2.

For example, the humidity in the first space SP1 may change by the influence of the external space through the opening 41*h* and the hole 12*h*. The second space SP2 is less susceptible to outside air than the first space SP1. Even when the humidity in the first space SP1 increases due to the influence of the outside air, the humidity in the second space SP2 is easily maintained low. In the embodiment, the first space SP1 is connected with the second space SP2. As a result, changes in humidity in the first space SP1 are suppressed by the second space SP2.

The detection characteristics of the sensor element 11 are affected by the state (for example, humidity) of the first space SP1. In the embodiment, the influence of substances other than the detection target gas 80 is reduced in the first space SP1. For example, the influence of humidity is reduced in the first space SP1. According to the embodiment, it is possible to provide a sensor capable of improving detection accuracy of the detection target gas 80.

In the embodiment, the volume of the second space SP2 is preferably equal to or greater than the volume of the first space SP1. The change in the state of the first space SP1 is more effectively reduced by the second space SP2.

As shown in FIGS. 1 and 2, the sensor 110 may further include a film member 31 being gas-permeable. The film member 31 includes an inner region 31*i* and an outer region 310. The outer region 310 is the region around the inner region 31*i*. The boundary between these regions may be clear or unclear. The outer region 310 is fixed to the first housing member 41. The sensor member 12 is located between the sensor element 11 and the inner region 31*i*. The detection target gas 80 can flow into the first space SP1 through the opening 41*h*, the film member 31 and the hole 12*h*.

For example, by providing the film member 31 suppress that water (liquid) enters the first space SP1. The film member 31 can suppress passage of liquid from the opening 41*h* to the first space SP1. For example, the first space SP1 is substantially waterproof.

The film member 31 preferably includes, for example, fluorine resin. For example, the film member 31 may include polytetrafluoroethylene. The entering of water is more effectively suppressed.

As shown in FIG. 1, the outer region 310 may be in contact with the first housing member 41. The inner region 31*i* may contact the sensor member 12.

As shown in FIG. 2, the sensor portion 10 may further include an element board 15 and a support portion 13. The sensor element 11 is located between the element board 15 and the sensor member 12. The support portion 13 is fixed to the element board 15. The support portion 13 is located between the element board 15 and the sensor member 12. The support portion 13 supports the sensor member 12.

A direction from the sensor element 11 to the sensor member 12 is defined as a first direction D1. the first direction D1 is defined as a Z-axis direction. One direction perpendicular to the Z-axis direction is defined as an X-axis direction. The direction perpendicular to the Z-axis direction and the X-axis direction is defined as a Y-axis direction.

The support portion 13 is provided around the sensor element 11 in a plane (X-Y plane) crossing the first direction D1 from the sensor element 11 to the sensor member 12. The element board 15, the support portion 13, the sensor member 12, and the film member 31 are provided around the first space SP1. For example, the first space SP1 is surrounded by the element board 15, the support portion 13, the sensor member 12, and the film member 31. A direction from the sensor element 11 to the support portion 13 is along a second direction D2. The second direction D2 crosses the first direction D1. The second direction D2 may be, for example, the X-axis direction or the Y-axis direction.

As shown in FIG. 2, for example, the sensor member 12 may be fixed to the support portion 13 via an electrode 13*e* provided on the support portion 13 and a sensor fixing portion 13*c*. The sensor fixing portion 13*c* is, for example, conductive paste.

As shown in FIG. 2, there is an area where the sensor fixing portion 13*c* is not provided. This area becomes the opening of the sensor portion 10 (sensor opening 10*h*). The sensor opening 10*h* connects the first space SP1 with the second space SP2. The sensor opening 10*h* serves as a path between the first space SP1 and the second space SP2.

Thus, the sensor portion 10 may include the sensor fixing portion 13*c*. The sensor fixing portion 13*c* fixes a part of the sensor member 12 to a part of the support portion 13. The sensor fixing portion 13*c* is not provided between another part of the sensor member 12 and another part of the support portion 13. The first space SP1 is connected to the second space SP2 through a space between the other part of the sensor member 12 and the other part of the support portion 13.

In the embodiment, it is preferable that the area of the path between the first space SP1 and the second space SP2 (cross-sectional area of the sensor opening 10*h*) is, for example, not less than 1/10 times and not more than 10 times the area (cross-sectional area) of the hole 12*h*. For example, the state (for example, humidity) of the first space SP1 tends to approach the state of the second space SP2. For example, highly accurate detection is possible while the influence of humidity is reduced.

As shown in FIG. 1, the housing 40 includes a second housing member 42 and a third housing member 43. The sensor portion 10 is provided between the third housing member 43 and the first housing member 41. The second housing member 42 is located around the sensor portion 10 in a plane (X-Y plane) crossing a direction (e.g., first direction D1) from the third housing member 43 to the first housing member 41. The second housing member 42 is connected to the first housing member 41 and the third housing member 43. The first housing member 41, the second housing member 42, and the third housing member 43 are provided around the second space SP2. For example, the second space SP2 is surrounded by the first housing member 41, the second housing member 42, and the third housing member 43. The second space SP2 is substantially waterproof.

As shown in FIG. 2, the housing 40 may further include a fourth housing member 44. The outer region 310 is located between the fourth housing member 44 and the first housing member 41. The outer region 310 is fixed by the fourth housing member 44 and the first housing member 41. For example, a fixing member 47 may be provided. The fixing member 47 fixes the fourth housing member 44 to the first housing member 41. The fixing member 47 is, for example, a screw.

As shown in FIG. 2, the sensor 110 may further include a first elastic member 46*a*. The first elastic member 46*a* is located between the outer region 310 and the first housing member 41. By providing the first elastic member 46*a*, the outer region 310 easily closely contact the first housing member 41. The first elastic member 46*a* is annular, for example. The first elastic member 46*a* may be an O-ring, for example. For example, the first elastic member 46*a* is of a resin.

As shown in FIG. 2, the sensor 110 may further include a second elastic member 46*b*. The second elastic member 46*b* is located between the fourth housing member 44 and the outer region 310. The second elastic member 46*b* is annular, for example. The second elastic member 46*b* may be an O-ring, for example. For example, the second elastic member 46*b* is of a resin.

The adhesive property of the film member 31 may be low. As described above, the film member 31 may be mechanically fixed by, for example, the fourth housing member 44, the first housing member 41, the first elastic member 46*a*, the second elastic member 46*b*, the fixing member 47, and the like. The film member 31 can be fixed with high adhesion even when the adhesion of the film member 31 is low. Entry of liquid into the sensor portion 10 from the outside can be suppressed. The sensor portion 10 can stably operate. High detection accuracy can be maintained.

As shown in FIGS. 1 and 2, the sensor portion 10 may include a first mounting board 16*a*. As shown in FIG. 2, the element board 15 is fixed to the first mounting board 16*a*. The first mounting board 16*a* may include various wiring layers. The wiring included in the element board 15 may be electrically connected to the wiring layer included in the first mounting board 16*a* by a connecting member 17*a* (for example, solder). The first mounting board 16*a* is, for example, a sensor board. In the sensor board, for example, a circuit capable of outputting sensor data in response to a request from a control board is provided. The control board is, for example, a microcomputer. For example, an IC (Integrated Circuit) may be provided on the sensor board. The IC may include, for example, an analog-to-digital converter 75*a*, a capacitance-to-digital converter 75*b*, or a DC/DC converter 75*c*.

As shown in FIG. 1, the sensor portion 10 may further include a second mounting board 16*b*. The first mounting board 16*a* is provided between the second mounting board 16*b* and the element board 15. A control circuit may be provided between the second mounting board 16*b* and the first mounting board 16*a*. The control circuit includes, for example, at least one of a microcomputer and a wireless communication circuit. The second mounting board 16*b* is provided with, for example, a circuit capable of controlling the IC provided on the first mounting board 16*a*.

As shown in FIG. 1, the first mounting board 16*a* may be fixed to the first housing member 41 by a structure body 48.

Figure 3:
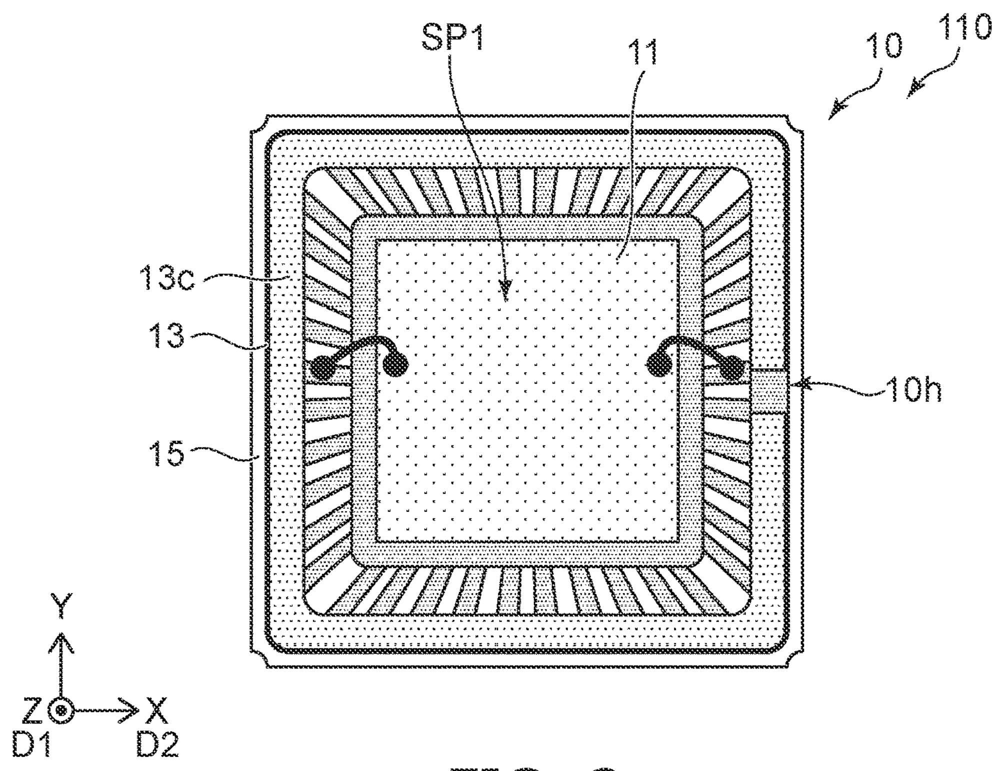
FIG. 3 is a schematic plan view illustrating a part of the sensor according to the first embodiment.

FIG. 3 is a schematic plan view illustrating a part of the sensor according to the first embodiment.

FIG. 3 illustrates the sensor portion 10. In FIG. 3, the sensor member 12 is omitted. As shown in FIG. 3, the sensor fixing portion 13*c* may be made of conductive paste, for example. In this example, there is an area where the sensor fixing portion 13*c* is not provided. This area becomes the sensor opening 10*h*. The first space SP1 is connected to the outside (second space SP2) through the sensor opening 10*h*. In the example of FIG. 3, the sensor fixing portion 13*c* has one continuous pattern shape.

Figure 4:
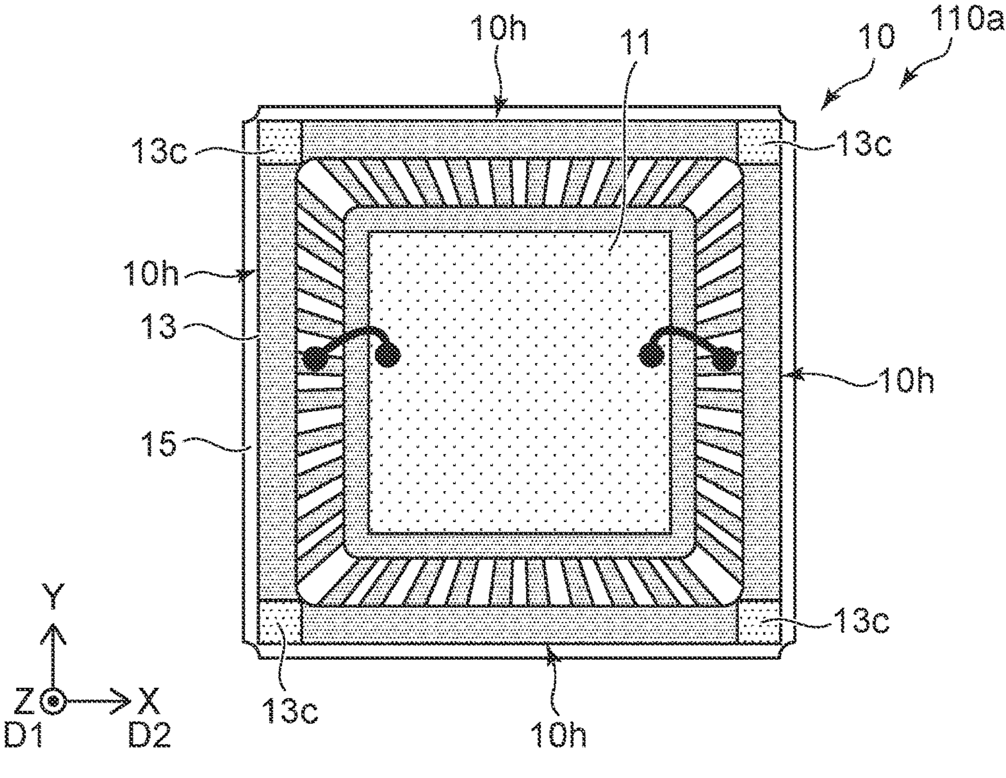
FIG. 4 is a schematic plan view illustrating a part of a sensor according to the first embodiment.

FIG. 4 is a schematic plan view illustrating a part of a sensor according to the first embodiment.

FIG. 4 illustrates the sensor portion 10 in a sensor 110*a* according to the embodiment. In FIG. 4, the sensor member 12 is omitted. As shown in FIG. 4, in the sensor 110*a*, a plurality of sensor fixing portions 13*c* (for example, conductive paste) are provided. A region between the sensor fixing portions 13*c* becomes the sensor opening 10*h*. A plurality of sensor openings may be provided. The first space SP1 is connected to the outside (second space SP2) through the plurality of sensor openings 10*h*. The plurality of sensor fixing portions 13*c* may be island-shaped. In the embodiment, the number and pattern shape of the sensor fixing portions 13*c* are arbitrary.

FIG. 5 is a schematic plan view illustrating a part of a sensor according to the first embodiment.

FIG. 5 illustrates the sensor portion 10 in a sensor 110*b* according to the embodiment. In FIG. 5, the sensor member 12 is omitted. As shown in FIG. 5, one continuous sensor fixing portion 13*c* is provided in the sensor 110*b*. In the X-Y plane, the first space SP1 is surrounded by the sensor fixing portion 13*c*. In this example, the sensor fixing portion 13*c* is porous. The sensor fixing portion 13*c* may be, for example, porous conductive paste. In the sensor 110*b*, the hole provided in the sensor fixing portion 13*c* functions as the sensor opening 10*h*.

Examples of characteristics of sensors are described below.

FIG. 6 is a graph illustrating characteristics of a sensor.

FIG. 6 illustrates the characteristics of a reference example in which the first space SP1 is not connected to the second space SP2. The horizontal axis of FIG. 6 is humidity H1 (% RH) of the first space SP1. The vertical axis is noise N1 (relative value) of the detection result of the sensor element 11. As shown in FIG. 6, when the humidity H1 increases, the noise N1 significantly increases. In the reference example, when the humidity in the first space SP1 increases by the influence of the outside air, the S/N ratio in detection of the detection target gas 80 decreases.

FIG. 7 is a graph illustrating sensor characteristics.

FIG. 7 illustrates characteristics when the first space SP1 is connected to the second space SP2. In the example of FIG. 7, the humidity in the outside air (the space outside the housing 40) is 90% RH. The humidity of the second space SP2 is 10% RH. The horizontal axis of FIG. 7 is the humidity H1 (% RH) of the first space SP1. The vertical axis is the S/N ratio of the detection result of the sensor element 11. The S/N ratio is standardized as 1 when the humidity H1 is 90% RH.

For example, the humidity H1 of the first space SP1 is determined by the size of the sensor opening 10*h* (or the volume ratio between the first space SP1 and the second space SP2, etc.).

For example, when the sensor opening 10*h* is extremely small, the humidity of the first space SP1 is approximately the same as the humidity of the outside air (90% RH). For example, when the volume of the second space SP2 is significantly smaller than the volume of the first space SP1, the humidity of the first space SP1 is approximately the same as the humidity of the outside air (90% RH). When the humidity H1 of the first space SP1 is high as about 90% RH, the S/N ratio is low.

On the other hand, for example, in the case where the sensor opening 10*h* is significantly large, the humidity H1 in the first space SP1 is substantially 10% RH under the influence of the second space SP2. For example, in the case where the volume of the second space SP2 is significantly larger than the volume of the first space SP1, the humidity H1 of the first space SP1 is substantially 10% RH due to the influence of the second space SP2. In such a case, the detection target gas 80 included in the first space SP1 flows out into the second space SP2, and the concentration of the detection target gas 80 in the first space SP1 decreases. For example, the rate of decrease in the concentration of the detection target gas 80 in the first space SP1 is linked to the rate of decrease in the humidity of the first space SP1 with respect to the humidity of the external space. Therefore, when the humidity H1 in the first space SP1 is approximately 10%, the S/N ratio is low. The case where the sensor opening 10*h* is significantly large includes the case where the sensor opening 10*h* is larger than the opening 41*h* of the first housing member 41.

For example, in the case where the sensor opening 10*h* has an appropriate size, the humidity H1 of the first space SP1 is lowered. The low humidity H1 reduces the noise N1. In the case where the sensor opening 10*h* has an appropriate size, the concentration of the detection target gas 80 in the first space SP1 does not become excessively low. In such a case, a high S/N ratio is obtained. In this example, the S/N ratio becomes a peak when the humidity H1 is approximately 50% RH.

When the humidity H1 becomes lower than about 50% RH, the S/N ratio decreases due to the decrease in the concentration of the detection target gas 80 in the first space SP1.

As described above, the humidity H1 in the first space SP1 is kept low by the second space SP2. On the other hand, the second space SP2 reduces the concentration of the detection target gas 80 in the first space SP1. The S/N ratio is determined by the effects of both the decrease in humidity in the first space SP1 and the decrease in concentration of the detection target gas in the first space SP1.

In the embodiment, a condition is applied in which the effect of reducing the concentration of the detection target gas in the first space SP1 is small. Thereby, a high S/N ratio is obtained.

For example, the area (cross-sectional area) of the sensor opening 10*h* is preferably not less than 1/10 times and not more than 10 times the area (cross-sectional area) of the hole 12*h*. For example, the low humidity H1 and the high concentration of the detection target gas 80 in the first space SP1 can be maintained. A high accuracy detection with low noise is possible.

For example, the first space SP1 is connected to the external space through the opening 41*h* of the first housing member 41 and the hole 12*h* of the sensor member 12. The second space SP2 is connected to the first space SP1 by an opening of the sensor portion 10 (sensor opening 10*h* or porous sensor fixing portion 13*c*).

The second space SP2 being larger than the first space SP1 is connected to the first space SP1 by the opening of the sensor portion 10 as described above.

In the embodiments, for example, the sensor element 11 may include a capacitive MEMS gas sensor. The sensor element 11 may include a thermal conductivity MEMS gas sensor. The sensor element 11 may include a contact combustion type MEMS gas sensor. The sensor element 11 may include an oxide semiconductor MEMS gas sensor. The sensor element 11 may include at least one of the plurality of gas sensors described above.

FIG. 8 is a schematic cross-sectional view illustrating the sensor according to the first embodiment.

As shown in FIG. 8, a sensor 111 according to the embodiment includes a dehumidifier 51. The configuration of the sensor 111 except for this may be the same as the configuration of the sensor 110. The dehumidifier 51 is configured to dehumidify the space inside the housing 40 (for example, the second space SP2). For example, the influence of humidity is suppressed, and the detection target gas can be detected with higher accuracy.

A porous member 32 may be provided between the external space and the dehumidifier 51. It is possible to suppress the liquid from adhering to the dehumidifier 51. The porous member 32 may include, for example, polytetrafluoroethylene. The porous member 32 may be fixed to housing 40 in any manner.

In this example, the sensor 111 includes a battery 53. The battery 53 is configured to supply power to the sensor portion 10.

In this example, a communicator 54 is provided. The communicator 54 is configured to transmit a signal based on a signal obtained from the sensor element 11 to the outside.

Figure 9:
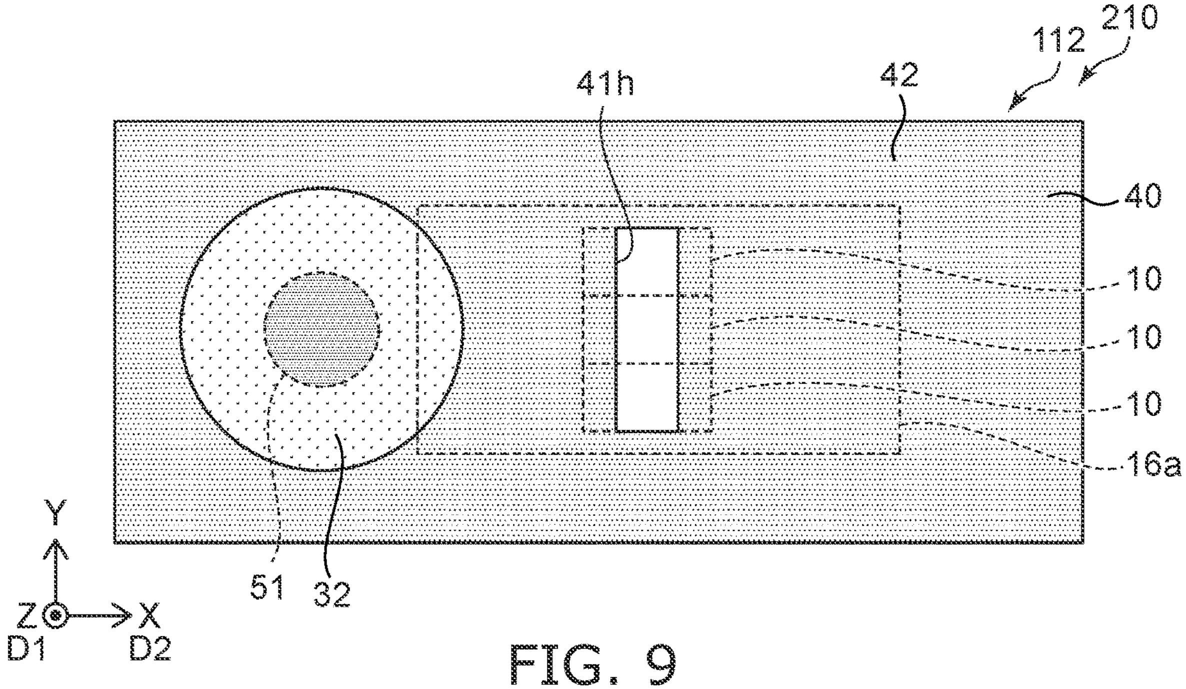
FIG. 9 is a schematic plan view illustrating the sensor according to the first embodiment.

FIG. 9 is a schematic plan view illustrating the sensor according to the first embodiment.

As shown in FIG. 9, a plurality of sensor portions 10 may be provided in a sensor 112 according to the embodiment. Except for this, the configuration of the sensor 112 may be the same as the configuration of the sensor 110, the sensor 110*a*, or the sensor 111. At least two of the plurality of sensor portions 10 may have different detection targets. For example, hydrogen may be detected by one of the multiple sensor portions 10 and carbon dioxide gas may be detected by another one of the multiple sensor portions 10.

Second Embodiment

The second embodiment relates to a sensor system. As shown in FIG. 8, the sensor system 210 according to the embodiment includes a sensor according to the embodiment (the sensor 110, the sensor 110*a*, the sensor 111, or the like) and the communicator 54. The control of the sensor may be performed via the communicator 54.

The embodiments may include the following configurations (for example, technical proposals).

Configuration 1

A sensor, comprising:

a housing including a first housing member, the first housing member including an opening;

a sensor portion provided in the housing, the sensor portion including a sensor member and a sensor element, the sensor member including a hole, a first space between the sensor element and the sensor member being connected to a second space in the housing, the second space being another space in the housing, a detection target gas being configured to flow into the first space through the opening and the hole.

Configuration 2

The sensor according to Configuration 1, wherein a volume of the second space is greater than or equal to a volume of the first space.

Configuration 3

The sensor according to Configuration 1 or 2, further comprising a film member being gas permeable, the film member including an inner region and an outer region around the inner region, the outer region being fixed to the first housing member, the sensor member being located between the sensor element and the inner region, and the detection target gas being configured to flow into the first space through the opening, the film member, and the hole.

Configuration 4

The sensor according to Configuration 3, wherein the outer region is in contact with the first housing member, and the inner region is in contact with the sensor member.

Configuration 5

The sensor according to Configuration 3 or 4, wherein the film member includes a fluorine resin.

Configuration 6

The sensor according to Configuration 3 or 4, wherein the film member includes polytetrafluoroethylene.

Configuration 7

The sensor according to any one of Configurations 3 to 6, wherein the sensor portion further includes an element board and a support portion, the sensor element is located between the element board and the sensor member, the support portion is fixed to the element board, the support portion is located between the element board and the sensor member, and the support portion supports the sensor member.

Configuration 8

The sensor according to Configuration 7, wherein the support portion is provided around the sensor element in a plane crossing a direction from the sensor element to the sensor member, and the element board, the support portion, the sensor member, and the film member are provided around the first space.

Configuration 9

The sensor according to Configuration 7 or 8, wherein the sensor portion includes a sensor fixing portion, the sensor fixing portion fixes a part of the sensor member to a part of the support portion, the sensor fixing portion is not provided between another part of the sensor member and another part of the support portion, and the first space is connected to the second space through a space between the other part of the sensor member and the other part of the support portion.

Configuration 10

The sensor according to any one of Configurations 3 to 9, wherein the film member is configured to suppress passage of liquid from the opening to the first space.

Configuration 11

The sensor according to any one of Configurations 3 to 10, wherein the first space is substantially waterproof.

Configuration 12

The sensor according to any one of Configurations 3 to 11, wherein the second space is substantially waterproof.

Configuration 13

The sensor according to any one of Configurations 3 to 12, further comprising a first elastic member, the first elastic member being provided between the outer region and the first housing.

Configuration 14

The sensor according to any one of Configurations 3 to 13, wherein the housing further includes a fourth housing member, the outer region is located between the fourth housing member and the first housing member, and the outer region is fixed by the fourth housing member and the first housing member.

Configuration 15

The sensor according to Configuration 14, further comprising a second elastic member, the second elastic member being located between the fourth housing member and the outer region.

Configuration 16

The sensor according to any one of Configurations 1 to 15, further comprising a dehumidifier, the dehumidifier being configured to dehumidify the second space.

Configuration 17

The sensor according to any one of Configurations 1 to 16, wherein the housing includes a second housing member and a third housing member, the sensor portion is located between the third housing member and the first housing member, the second housing member is provided around the sensor portion in a plane crossing a first direction from the third housing member to the first housing member, the second housing member is connected to the first housing member and the third housing member, and the first housing member, the second housing member, and the third housing member are provided around the second space.

Configuration 18

The sensor according to any one of Configurations 1 to 17, wherein a first gas permeability between the first space and an external space is lower than a second gas permeability between the first space and the second space.

Configuration 19

The sensor according to any one of Configurations 1 to 18, wherein the sensor element includes at least one of a capacitive MEMS gas sensor, a thermal conductivity MEMS gas sensor, a contact combustion type MEMS gas sensor, or an oxide semiconductor MEMS gas sensor.

Configuration 20

A sensor system, comprising;

the sensor according to any one of Configurations 1 to 19; and a communicator, the communicator being configured to transmit a signal based on a signal obtained from the sensor element to the outside.

According to the embodiments, it is possible to provide a sensor and a sensor system capable of improving detection accuracy.

Hereinabove, exemplary embodiments of the invention are described with reference to specific examples. However, the embodiments of the invention are not limited to these specific examples. For example, one skilled in the art may similarly practice the invention by appropriately selecting specific configurations of components included in sensors and sensor systems such as housings, sensor portions, sensor element, film members, etc., from known art. Such practice is included in the scope of the invention to the extent that similar effects thereto are obtained.

Further, any two or more components of the specific examples may be combined within the extent of technical feasibility and are included in the scope of the invention to the extent that the purport of the invention is included.

Moreover, all sensors and sensor systems practicable by an appropriate design modification by one skilled in the art based on the sensors and the sensor systems described above as embodiments of the invention also are within the scope of the invention to the extent that the purport of the invention are included.

Various other variations and modifications can be conceived by those skilled in the art within the spirit of the invention, and it is understood that such variations and modifications are also encompassed within the scope of the invention.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the invention.

What is claimed is:

1. A sensor, comprising:

a housing including a first housing member, the first housing member including an opening;

a sensor portion provided in the housing, the sensor portion including a sensor member and a sensor element, the sensor member including a hole, a first space between the sensor element and the sensor member being connected to a second space in the housing, the second space being another space in the housing, a detection target gas being configured to flow into the first space through the opening and the hole; and a film member being gas permeable, the film member including an inner region and an outer region around the inner region, the outer region being fixed to the first housing member, the sensor member being located between the sensor element and the inner region, and the detection target gas being configured to flow into the first space through the opening, the film member, and the hole, wherein the sensor portion further includes an element board and a support portion, the sensor element is located between the element board and the sensor member, the support portion is fixed to the element board, the support portion is located between the element board and the sensor member, and the support portion supports the sensor member, at least a part of the support portion is provided around the sensor element in a plane crossing a first direction from the sensor element to the sensor member,
the sensor portion includes a sensor fixing portion,
the sensor fixing portion fixes a part of the sensor member to a part of the support portion,
the sensor fixing portion is not provided between another part of the sensor member and another part of the support portion to form a sensor opening extending along a direction crossing the first direction,
a direction from the part of the sensor member to the other part of the sensor member is along the plane,
a direction from the part of the support portion to the other part of the support portion is along the plane, and
the first space is connected to the second space through the sensor opening.

2. The sensor according to claim 1, wherein a volume of the second space is greater than or equal to a volume of the first space.

3. The sensor according to claim 1, wherein
the outer region is in contact with the first housing member, and
the inner region is in contact with the sensor member.

4. The sensor according to claim 1, wherein the film member includes a fluorine resin.

5. The sensor according to claim 1, wherein the film member includes polytetrafluoroethylene.

6. The sensor according to claim 1, wherein
the element board, the support portion, the sensor member, and the film member are provided around the first space.

7. The sensor according to claim 1, wherein the film member is configured to suppress passage of liquid from the opening to the first space.

8. The sensor according to claim 1, wherein the first space is substantially waterproof.

9. The sensor according to claim 1, wherein the second space is substantially waterproof.

10. The sensor according to claim 1, further comprising a first elastic member,
the first elastic member being provided between the outer region and the first housing.

11. The sensor according to claim 1, wherein
the housing further includes a fourth housing member,
the outer region is located between the fourth housing member and the first housing member, and
the outer region is fixed by the fourth housing member and the first housing member.

12. The sensor according to claim 11, further comprising a second elastic member,
the second elastic member being located between the fourth housing member and the outer region.

13. The sensor according to claim 1, further comprising a dehumidifier,
the dehumidifier being configured to dehumidify the second space.

14. The sensor according to claim 1, wherein
the housing includes a second housing member and a third housing member,
the sensor portion is located between the third housing member and the first housing member,
the second housing member is provided around the sensor portion in the plane,
the second housing member is connected to the first housing member and the third housing member, and
the first housing member, the second housing member, and the third housing member are provided around the second space.

15. The sensor according to claim 1, wherein a first gas permeability between the first space and an external space is lower than a second gas permeability between the first space and the second space.

16. The sensor according to claim 1, wherein the sensor element includes at least one of a capacitive MEMS gas sensor, a thermal conductivity MEMS gas sensor, a contact combustion type MEMS gas sensor, or an oxide semiconductor MEMS gas sensor.

17. A sensor system, comprising;
the sensor according to claim 1; and
a communicator,
the communicator being configured to transmit a signal based on a signal obtained from the sensor element to the outside.

18. The sensor according to claim 1, wherein
the detection target gas flows to the second space through the first space after passing the first space through the film member.

19. A sensor, comprising: a housing including a first housing member, the first housing member including an opening; a sensor portion provided in the housing, the sensor portion including a sensor member and a sensor element, the sensor member including a hole, a first space between the sensor element and the sensor member being connected to a second space in the housing, the second space being another space in the housing, a detection target gas being configured to flow into the first space through the opening and the hole; and a film member being gas permeable, the film member including an inner region and an outer region around the inner region, the outer region being fixed to the first housing member, the sensor member being located between the sensor element and the inner region, and the detection target gas being configured to flow into the first space through the opening, the film member, and the hole, wherein the sensor portion further includes an element board and a support portion, the sensor element is located between the element board and the sensor member, the support portion is fixed to the element board, the support portion is located between the element board and the sensor member, and the support portion supports the sensor member, at least a part of the support portion is provided around the sensor element in a plane crossing a first direction from the sensor element to the sensor member, the sensor portion includes a sensor fixing portion, the sensor fixing portion fixes a part of the sensor member to a part of the support portion, the first space is connected to the second space through a sensor opening extending along a direction crossing the first direction provided in the support portion.

* * * * *